United States Patent [19]

Goodley

[11] Patent Number: 4,851,700
[45] Date of Patent: Jul. 25, 1989

[54] ON-AXIS ELECTRON ACCELERATION ELECTRODE FOR LIQUID CHROMATOGRAPHY/MASS SPECTROMETRY

[76] Inventor: Paul C. Goodley, 19990 Brenda Ct., Cupertino, Calif. 95014

[21] Appl. No.: 194,591

[22] Filed: May 16, 1988

[51] Int. Cl.[4] .......................................... D01D 59/44
[52] U.S. Cl. ................................... 250/288; 250/281; 250/423 R
[58] Field of Search ................... 250/281, 288, 288 A, 250/428, 432 R

[56] References Cited

U.S. PATENT DOCUMENTS

| | | | |
|---|---|---|---|
| 3,997,298 | 12/1976 | McLafferty et al. | 23/253 R |
| 4,546,253 | 10/1985 | Tsuchiya et al. | 250/288 A |
| 4,647,772 | 3/1987 | Lewis et al. | 250/288 |
| 4,667,100 | 5/1987 | Lagna | 250/281 |

OTHER PUBLICATIONS

Vestal, M. L., "Studies of Ionization Mechanisms Involved in Thermospray LC-MS", *International Journal of Mass Spectrometry and Ion Physics*, 46 (1983), pp. 193-196.

*Primary Examiner*—Janice A. Howell
*Assistant Examiner*—Michael Aronoff
*Attorney, Agent, or Firm*—Robert P. Sabath

[57] ABSTRACT

An improved liquid chromatography/mass spectrometer apparatus is disclosed of the type wherein the liquid eluent from a chromatograph column is injected as a heated spray into an ionization chamber located between the chromatograph and the mass spectrometer to form ionized adducts containing solvent and the molecule to be analyzed which are then passed into the mass spectrometer through an exit port in the sidewall of the ionization chamber. The improvement comprises an acceleration electrode located in the sidewall of the ionization chamber at a position opposite the exit port into the mass spectrometer, an electron emission source located between the acceleration electrode and the point of injection of the heated spray into the chamber, and means for providing a positive voltage on the acceleration electrode with respect to the electron emission source in the ionization chamber. The acceleration electrode is maintained at a voltage sufficiently high to permit a stream of electrons flowing from the electron emission source to the acceleration electrode to bombard the heated spray to form hydronium ions, and fragment at least a portion of the molecules being analyzed into two or more lower molecular weight constituents or molecular ions to thereby aid in identification of the molecule.

20 Claims, 4 Drawing Sheets

ON-AXIS ELECTRON ACCELERATION ELECTRODE FOR LIQUID CHROMATOGRAPHY/MASS SPECTROMETRY

BACKGROUND OF THE INVENTION

1. Field of the Invention

This invention relates to improved apparatus for analysis of compounds by liquid chromatography/mass spectrometry. More particularly, this invention relates to apparatus which will provide a stream of electrons flowing in the ionization chamber of the mass spectrometer in the same direction as the spray of liquid/vapor from the liquid chromatograph and at an energy level sufficient to: (1) bombard gaseous molecules which form ions and fragment ions; and (2) form hydronium ions which act as reagent ions for further ionization of the molecules in the spray.

2. Description of the Related Art

The analysis of molecules of decomposable liquids or solids, using liquid chromatographic-mass spectrometry apparatus is known wherein the liquid eluent containing the molecule to be analyzed is sprayed into an ionization chamber, juxtapositioned between the chromatographic column and the mass spectrometer, and formed therein into an ionized adduct by ionization of the solvent in the spray through exposure to a beam of high energy electrons also introduced into the ionization chamber. Typical of such apparatus is the liquid chromatography mass spectrometry system disclosed in McLafferty et al U.S. Pat. No. 3,997,298.

Another system used in liquid chromatography-mass spectrometry analysis of decomposable molecules is the thermospray method wherein an ionized solvent, e.g., ammonium acetate, is used with the liquid/solid compound to be analyzed. The liquid eluent from the chromatograph column containing such an ionized solvent is introduced into the ionization chamber through one or more heated nozzles. The ions already present in the solution evaporate in solvated form from droplets in the thermally produced spray. For example, if the solution being analyzed comprises a compound dissolved in the aforementioned ammonium acetate solvent, the ammonium and acetate ions formed in the spray may form ionized adducts with the compound which ionized adducts may then be analyzed in the mass spectrometer. This thermospray form of ionization of liquids is described by M. L. Vestal in the International Journal of Mass Spectrometry and Ion Physics, 1983, Vol. 46, at pp. 193-196.

In such an apparatus, the thermospray is introduced through one or more heated nozzles into one end of an ionization chamber having an exit port to a vacuum pump at the opposite end whereby the solvent-spray will flow toward the exit port of the ionization chamber. At a point in the sidewall of the ionization chamber, spaced from the entrance nozzle and the exit port, is an opening, which may comprise a cone depending from the sidewall into the ionization chamber with an opening at the apex of the cone. The ionized adducts pass through this opening into the mass spectrometer which is maintained at a higher vacuum (lower pressure).

Flow of the ionized adducts through the opening in the sidewall of the ionization chamber into the mass spectrometer involves a change in direction of the flow of the ionized adducts influenced by the higher vacuum at the mass spectrometer entrance on these ionized adducts. Thus some fraction of the material to be analyzed flows into the mass spectrometer while most of the vaporized solvent passes on to the exit port at the end of the ionization chamber to the vacuum pump connected thereto.

To assist in this separation of the ions - or ionized adducts - to be analyzed from the remainder of the solvent, it has been proposed by Lewis et al, in U.S. Pat. No. 4,647,772, to locate a "repeller" electrode in the ionization chamber downstream of the opening in the sidewall to the mass spectrometer. This "repeller" electrode is maintained at a potential sufficient to provide a repulsive electrostatic field in the ionization chamber which will retard the flow of ionized adducts in the chamber and deflect the flow to the opening in the chamber into the mass spectrometer.

While such modifications have improved the analysis of decomposable liquids and solvents by the liquid chromatography/mass spectrometry method, the method, in the main, is still limited to ascertaining the molecular weight of the unknown compound and using this to identify the compound. It would, therefore, be desirable to be able to fragment the unknown molecule, as in gas chromatography/mass spectrometry systems, to provide further information as to the structure of the unknown molecule by identification of peaks associated with fragmented groups of the molecule.

SUMMARY OF THE INVENTION

It is, therefore, an object of this invention to provide an improved apparatus for the analysis of liquid/solid compounds by liquid chromatography/mass spectrometry comprising an electron accelerating electrode located in the ionization chamber opposite the opening therefrom to the mass spectrometer and maintained at a potential sufficient to provide a flow of electrons in the chamber which will fragment the molecules and ionized adducts into smaller molecules and smaller ions.

It is another object of this invention to provide an improved apparatus for the analysis of liquid/solid compounds by liquid chromatography/mass spectrometry comprising an accelerating electrode located in the ionization chamber opposite the opening therefrom to the mass spectrometer and an electron emission source in the chamber between the entrance to the chamber and the opening to the mass spectrometer with the accelerating electrode maintained at a potential, with respect to the electron emission source, sufficient to provide a flow of electrons from the electron emission source to the accelerating electrode which will fragment the molecules and the ionized adducts into smaller molecules and smaller ions.

It is yet another object of this invention to provide an improved apparatus for the analysis of liquid/solid compounds by liquid chromatography/mass spectrometry comprising an accelerating electrode located in the ionization chamber opposite the opening therefrom to the mass spectrometer, an electron emission source in the chamber between the entrance to the chamber and the opening to the mass spectrometer, and means for maintaining the accelerating electrode at a potential, with respect to the electron emission source, sufficient to provide a flow of electrons from the electron emission source to the accelerating electrode which will fragment the molecules and the ionized adducts into smaller molecules and smaller ions.

These and other objects of the invention will be apparent from the following description and accompanying drawings.

DETAILED DESCRIPTION OF THE INVENTION

The invention provides improved apparatus for a liquid chromatography/mass spectrometry system wherein the ionization chamber located between the chromatograph column and the mass spectrometer analyzer is provided with an accelerating electrode opposite the opening from the chamber into the mass spectrometer and an electron emission source of electrons between the entrance into the chamber and the opening to the mass spectrometer to permit establishment of a flow of electrons therebetween of sufficient potential to fragment the molecules to be analyzed into smaller portions to assist in identifying the molecule by providing ion peaks in the mass spectrometer data corresponding to the respective fragments.

Figure 1:
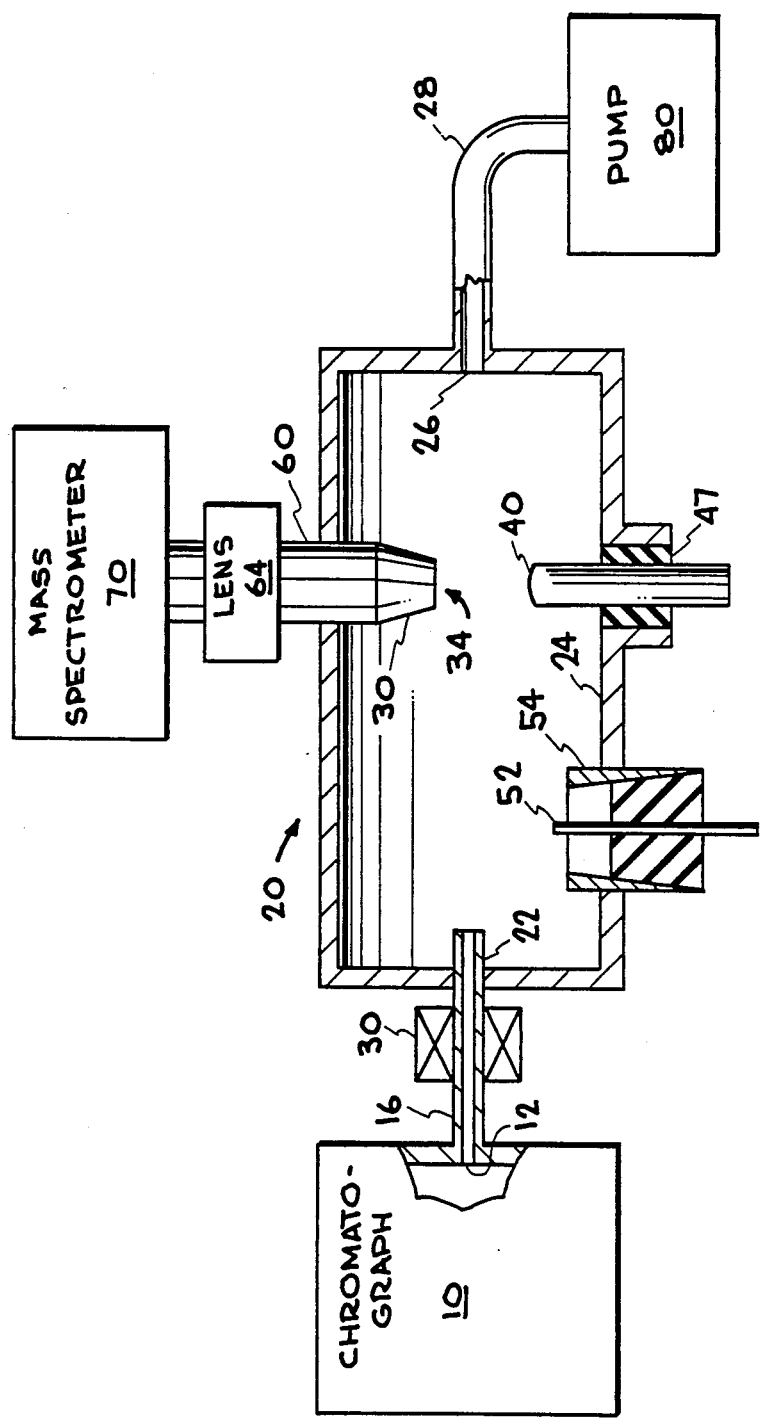
FIG. 1 is a schematic illustration of the improved apparatus of the invention showing its position in general in the liquid chromatography/mass spectrometry system to which the invention applies.

Referring now to FIG. 1, an embodiment of the improved apparatus of the invention is schematically depicted by way of illustration and not of limitation comprising a chromatograph column 10 having an outlet 12 through which eluent flows to an elongated cylinder comprising ionization chamber 20 via pipe or tube 16. Heating means 30 are provided around tube 16 to heat the eluent therein sufficiently as it passes through tube 16 so that the solvent portion of the eluent will at least partially vaporize as it is sprayed into chamber 20 via nozzle 22 which is preferably located coaxially in the end wall of cylindrical chamber 20.

Chamber 20 is provided, at the opposite end from entrance nozzle 22, with an exit port 26 which leads to a vacuum pump 80 via conduit 28 to maintain a vacuum of about 0.05 to 10 Torr in ionization chamber 20.

At an intermediate point in chamber 20 between nozzle 22 and exit port 26 is located a cone shaped member 30 which depends into chamber 20 from sidewall 24 thereof. Cone member 30 is situated so that its apex, which comprises an opening 34, terminates approximately at the center axis of cylindrical ionization chamber 20.

Opening 34 in cone 30 provides an entrance to mass spectrometer 70 via a passageway 60 which may lead through an electrostatic lens 64 to focus the beam of ions as it enters mass spectrometer 70.

Spectrometer 70 may comprise any type of mass spectrometer such as, for example a single-focusing magnetic sector analyzer, a double focusing magnetic sector analyzer, a quadrapole spectrometer, or any other type of mass spectrometer capable of resolving and quantitatively measuring a beam of ions based on their mass-to-charge ratios.

Figure 2A:
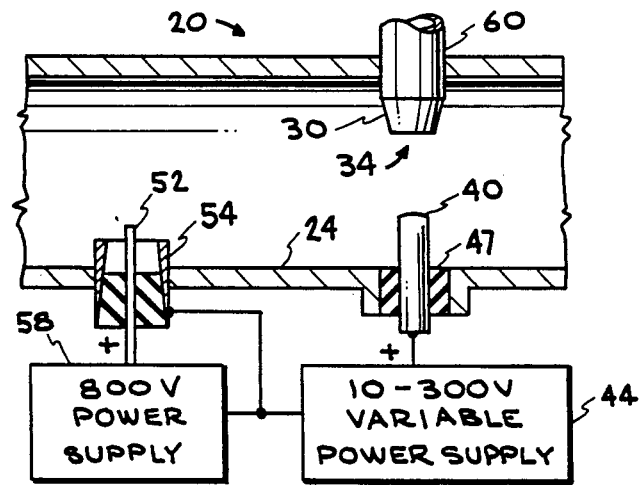
FIGS. 2A–2C are fragmentary vertical cross-sectional views of alternate embodiments of the invention.
Figure 2B:
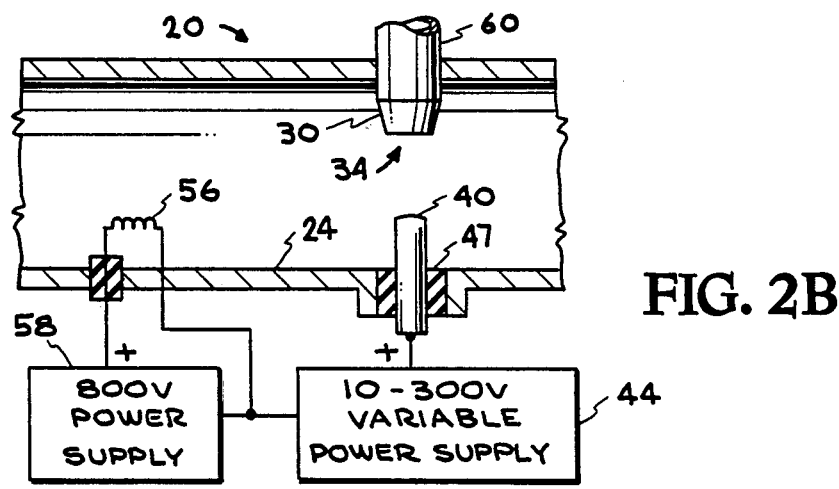
Figure 2C:
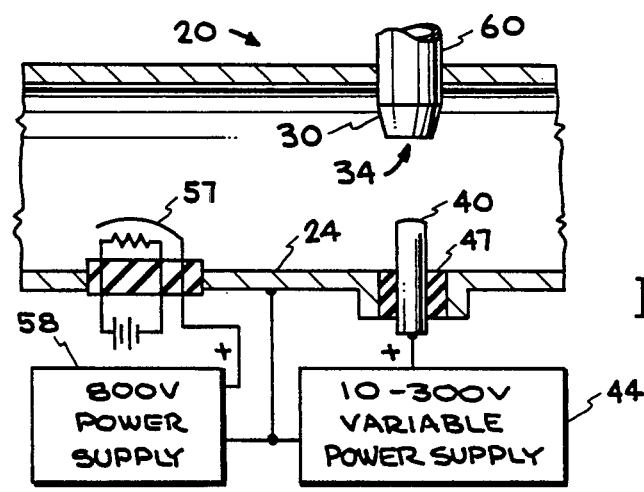

Still referring to FIG. 1, as well as FIGS. 2A–2C, in accordance with the invention, ionization chamber 20 is further provided with an acceleration electrode 40 which is insulatively mounted in sidewall 24 of chamber 20 opposite opening 34 in cone 30. Electrode 40, in a preferred embodiment, comprises a metal rod having a semispherical end thereon, having a radius at the semispherical end, of from about 0.05 to about 0.100 inches, preferably 0.0625 inch, which extends into the ion volume of the ion source column, i.e., the semispherical end of electrode 40, extends into cylinder 20 normal to the sidewall a distance sufficient to intersect the spray of analyte traveling down the axis of cylindrical chamber 20.

This will usually comprise extending electrode 40 into chamber 20 a distance of from about 5 to about 50% of the diameter of chamber 20, preferably from about 10 to about 25%, and most preferably from about 15 to about 20%. The total exposed area of electrode 40 within chamber 20 is sufficient to provide a field of between about $10^3$ to about $10^6$ volts per square centimeter.

Electrode 40 is insulated from sidewall 24 by appropriate insulation means 47 capable of withstanding the voltage to be applied to electrode 40 with respect to sidewall 24 which is maintained at a ground or neutral potential with respect to electrode 40. Insulation means 47 may comprise a ceramic collar, such as, for example, an alumina or silica collar, bonded to both sidewall 24 and electrode 40 to provide a vacuum tight seal therebetween.

Electrode 40 is connected to a variable positive voltage source 44 to provide a positive potential thereon, with respect to sidewall 24 of chamber 20, of from about 10 to about 300 volts, preferably from about 20 to about 260 volts, although higher voltages may be used if needed or desired. The minimum or threshold voltage applied to electrode 40, as will be discussed below, will differ depending upon the particular reaction parameters used.

Upstream of electrode 40 and cone 30 in chamber 20, located between entrance nozzle 22 and electrode 40, is an electron emission source or cathode. The electron emission source may comprise a glow discharge type electrode maintained at a high voltage, e.g., from about 600 to about 1000 volts, preferably about 800 volts, with respect to sidewall 24 of chamber 20, such as electrode 52 shown in FIGS. 1 and 2A, at least partially surrounded by an electrode 54 electrically connected to sidewall 24; or a direct filament cathode 56, as shown in FIG. 2B; or an indirectly heated cathode 57, such as shown in FIG. 2C. In any case, the electron emission source is electrically connected to a power source 58.

It should be noted, however, at this point that the electron emission source should be located within chamber 20, as opposed to comprising an externally produced beam of electrons which is merely introduced into chamber 20 at a point between entrance nozzle 22 and electrode 40. It has been found that an externally produced beam of electrons introduced into chamber 20 as a beam of electrons will not produce the desired electron flow toward electrode 40, i.e., will not produce a flow of electrons generally flowing in the same direction as the ionized adducts or droplets.

As mentioned above, the minimum voltage to be applied to electrode 40 will depend upon the particular reaction parameters used, including the vacuum within chamber 20, and the particular liquids being analyzed, including the solvents used. While the actual minimum voltage will not, therefore, always be the same value, the needed minimum voltage used under any particular conditions may be easily ascertained by monitoring the presence of the hydronium ion in the mass spectrometer, as will now be explained.

When an ionizable solvent is used, such as water, in the particular type of liquid chromatography/mass spectrometry apparatus to which the invention applies, water molecules are present in the spray which is bombarded by the electron beam or flow established between the electron emission source and electrode 40. When the electron flow is sufficiently high, the molecules in the ionized spray will be fragmented into smaller ions. At the same time, the water molecules will also be bombarded by the electron stream resulting in the production of hydronium ions as shown in the following equations which illustrate, respectively, the bombarding of the water molecules with electrons to form water ions and the collision of the resulting charged water ions with further water molecules to form the charged hydronium ion:

  (1)

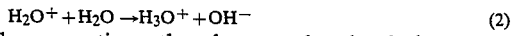  (2)

At the same time, the electrons bombard the vapor phase molecules of the unknown compound, i.e., the analyte, fragmenting the molecules into smaller molecules and ions as shown in the following equation wherein M represents the molecule being bombarded and A, B, and C represent the fragmented charged portions of molecule M.

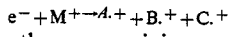

Since the same minimum potential is needed for the electron stream to produce the hydronium ion by bombardment of water molecules as is needed to fragment the unknown molecule, monitoring for the appearance of the hydronium ion in quantity can be used to determine the potential needed to fragment the unknown molecule. This, in turn, can be used to indicate the potential at which one analyzing the mass spectrometer data should look for the presence of significant amounts of molecules at molecular weights indicative of such fragmentation and is used as an indicator of the energy needed for fragmentation.

Figure 3A:
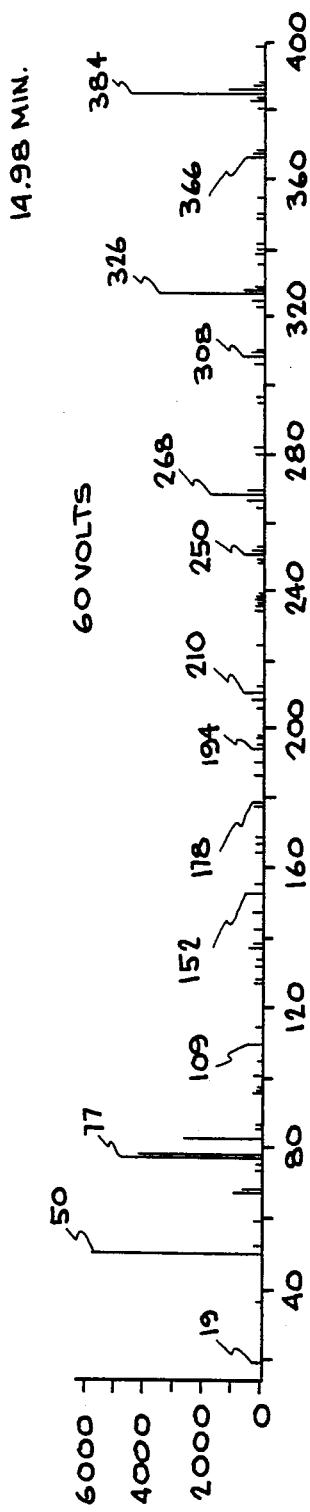
FIG. 3A is a graph showing the mass spectrometer data with the accelerating electrode operating at a potential below the potential sufficient to establish a flow of electrons capable of forming the hydronium ion from water molecules.
Figure 3B:
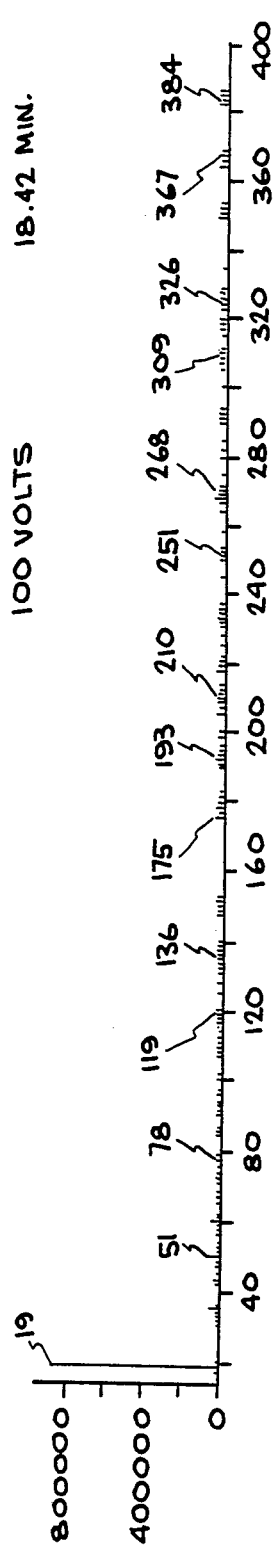
FIG. 3B is a graph showing the mass spectrometer data with the accelerating electrode operating at a potential sufficient to form hydronium ions from the water molecules present in the analyte.

This is illustrated in the graphs of FIGS. 3A and 3B wherein it is shown that operating electrode 40 at a potential of 60 volts does not result in the detection of any significant amount of hydronium ion (molecular weight or atomic weight 19) being produced by bombardment of the spray by the flow of electrons produced at this potential, as shown in FIG. 3A.

In contrast, however, as shown in FIG. 3B, when the potential on electrode 40 is raised to 100 volts, the hydronium ion is detected in large quantity (15,000 times greater), which shows that the energy level of the electron flow is sufficient to fragment molecules with which the high energy electrons collide as the electrons flow from the electron emission source to electrode 40.

Figure 4A:
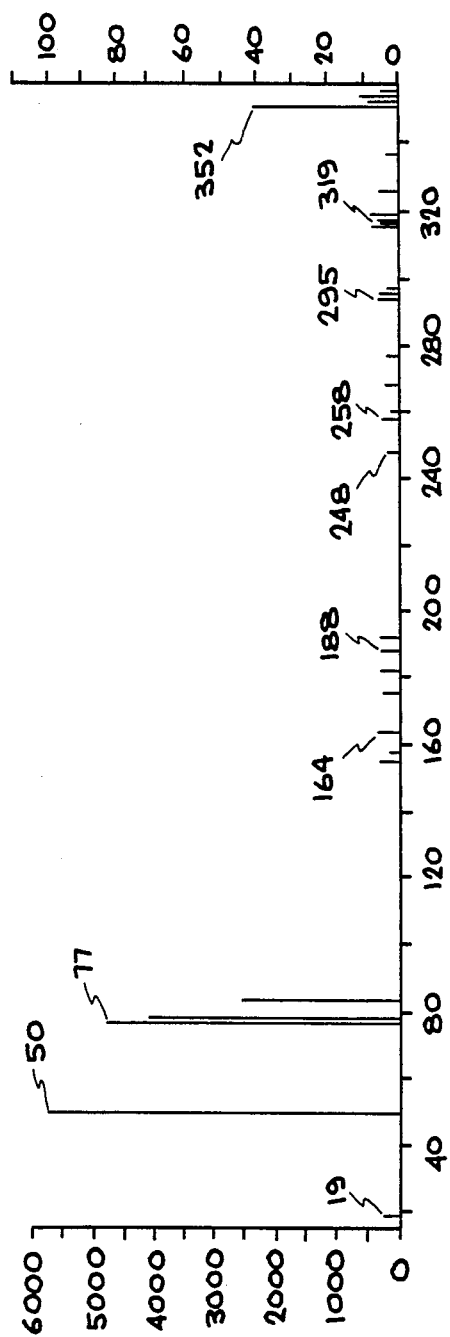
FIG. 4A is a graph showing the mass spectrometer data for an analyte containing a tripeptide of molecular weight 351 with the accelerating electrode not operating.

To further illustrate the invention, a solution containing a tripeptide having an atomic mass of 351 grams (352 grams with hydrogen attached) comprising glycine, leucine, and tyrocine in an ammonium acetate solvent was sprayed into an ionization chamber of a liquid chromatography/mass spectrometry apparatus constructed in accordance with the invention. At first no voltage was applied to electrode 40. As can be seen in FIG. 4A, very little hydronium ion was detected as present in the mass spectrometer, as evidenced by the absence of a peak at atomic mass 19. Correspondingly, as also seen in FIG. 4A, a peak at 352, indicative of the peptide molecule, as well as the absence of peaks at 171 and 182, indicates that for this system, in the absence of a potential on electrode 40, not only are hydronium ions not produced from the water molecules present, but the tripeptide molecules are not fragmented either.

Figure 4B:
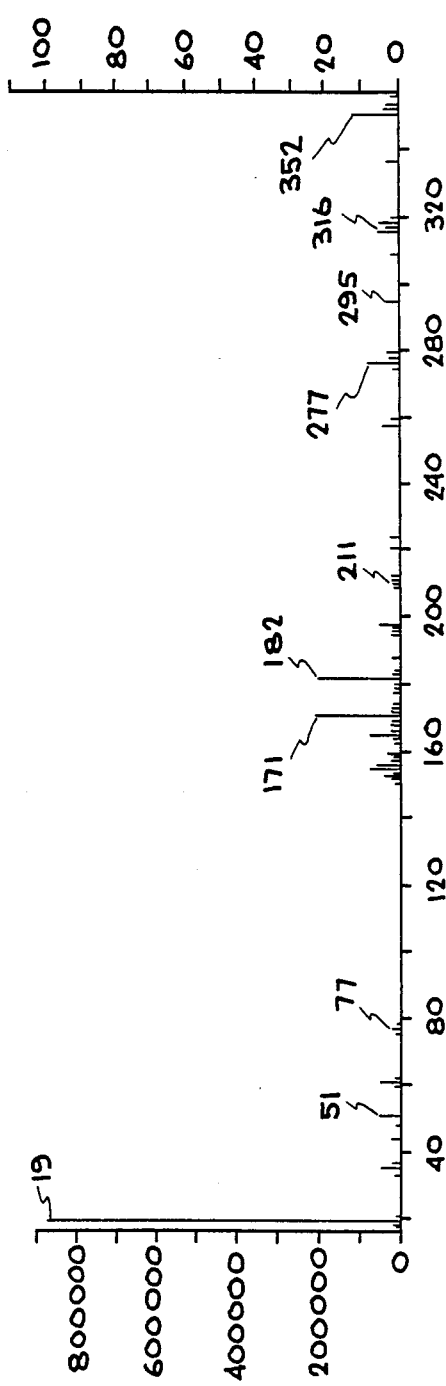
FIG. 4B is a graph showing the mass spectrometer data indicating the presence of hydronium ions for the same analyte as in FIG. 4A but with the accelerating electrode operating at a potential sufficient to establish a flow of electrons which form hydronium ions from the water molecules present in the analyte and to fragment the tripeptide into smaller molecules or fragments having peaks at 171 and 182.

In contrast, as shown in the graph of FIG. 4B, when the same solution was sprayed into the ionization chamber with electrode 40 maintained at a potential sufficient that the resulting flow of electrons from electron emission source 50 to electrode 40 produced hydronium ions, the tripeptide molecules were also fragmented. This is shown, respectively, in FIG. 4B by the peak at 19, indicating the presence of the hydronium ion, and the peaks at 171 and 182, indicating that tripeptide molecules were fragmented into smaller molecules having molecular weights consistent with the expected weights of the respective fragments or portions which would result if the tripeptide fragmented at the points where it would be most likely expected to split.

Thus, the invention provides means for fragmenting molecules being analyzed by liquid chromatography/mass spectrometry apparatus whereby further data may be obtained using this analytical method indicative not only the molecular weight of the unknown molecule, but also of the possible structure of the molecule, based on fragmenting of particular molecules at certain predictable points in the molecular structure. The detection of the presence or absence of a peak at 19 indicative of the formation of hydronium ions from water molecules at the same potential provides a easy means for determining whether the potential on electrode 40 is sufficient to provide fragmentation of the unknown molecules in the analyte.

Having thus described the invention, what is claimed is:

1. In a liquid chromatography/mass spectrometer apparatus wherein liquid eluent from a chromatograph is injected as a heated spray into an ionization chamber located between the chromatograph and the mass spectrometer to form ionized adducts containing solvent and the molecule to be analyzed which are then passed into said mass spectrometer through an exit port in the sidewall of said ionization chamber, the improvement which comprises:

(a) an acceleration electrode located in the sidewall of said ionization chamber at a position opposite said exit port into said mass spectrometer;

(b) an electron emission source located between said acceleration electrode and the point of injection of said heated spray into said chamber; and
(c) means for providing a positive voltage on said acceleration electrode with respect to said sidewall of said ionization chamber;

whereby the potential on said acceleration electrode may be raised to a voltage sufficiently high to permit a stream of electrons flowing from said electron emission source to said acceleration electrode to bombard said heated spray to fragment at least a portion of said molecules being analyzed into two or more lower molecular weight constituents to thereby aid in identification of said molecules.

2. The apparatus of claim 1 wherein said acceleration electrode has a semispherical end positioned in said chamber.

3. The apparatus of claim 2 wherein said semi-radius end of said acceleration electrode has a radius of from about 0.05 to about 0.100 inches.

4. The apparatus of claim 3 wherein said semispherical end of said acceleration electrode has a radius of about 0.0625 inches.

5. The apparatus of claim 1 wherein said ionization chamber comprises a cylindrical chamber and said liquid eluent injected as a heated spray into said ionization chamber is coaxially injected into one end of said chamber.

6. The apparatus of claim 5 wherein said acceleration electrode protrudes through the sidewall of said cylindrical ionization chamber a distance of about 5 to about 50% of the diameter of said cylindrical ionization chamber, whereby said electrons flowing from said electron emission source to said accelerating electrode will generally coincide with said spray of eluent traveling through said chamber.

7. The apparatus of claim 6 wherein said acceleration electrode protrudes through the sidewall of said cylindrical ionization chamber a distance of about 10 to about 25% of the diameter of said cylindrical ionization chamber.

8. The apparatus of claim 7 wherein said acceleration electrode protrudes through the sidewall of said cylindrical ionization chamber a distance of about 15 to about 20% of the diameter of said cylindrical ionization chamber.

9. The apparatus of claim 1 wherein said electron emission source comprises a direct filament cathode and said means for supplying a positive voltage on said accelerating electrode are electrically connected between said accelerating electrode and said sidewall.

10. The apparatus of claim 1 wherein said electron emission source comprises a glow discharge type electrode at least partially surrounded by a second electrode electrically connected to the sidewall of the chamber and said means for supplying a positive voltage on said accelerating electrode are electrically connected between said accelerating electrode and said sidewall.

11. The apparatus of claim 1 wherein said electron emission source comprises an indirect heated cathode and said means for supplying a positive voltage on said accelerating electrode are electrically connected between said accelerating electrode and said sidewall.

12. The apparatus of claim 1 wherein said means for providing a positive voltage on said acceleration electrode comprise a power supply means capable of adjustment whereby the potential on said accelerating electrode may be raised until the presence of a peak is detected by said mass spectrometer indicating the presence of hydronium ions formed from water molecules present in said liquid eluent.

13. The apparatus of claim 12 wherein the potential on said accelerating electrode varies from about 10 to about 300 volts positive with respect to said sidewall.

14. The apparatus of claim 13 wherein the potential on said accelerating electrode varies from about 20 to about 260 volts positive with respect to said sidewall.

15. In a liquid chromatography/mass spectrometer apparatus wherein liquid eluent from a chromatograph is coaxially injected as a heated spray into the end of a cylindrical ionization chamber located between the chromatograph and the mass spectrometer to form ionized adducts containing solvent and the molecule to be analyzed which are then passed into said mass spectrometer through an exit port in the sidewall of said cylindrical ionization chamber, the improvement which comprises:
(a) an acceleration electrode, having a semispherical end thereon, insulatively mounted in the sidewall of said ionization chamber and protruding normally into said cylindrical ionization chamber a distance of about 10 to about 25% of the diameter of said cylindrical chamber, said electrode located at a position opposite said exit port into said mass spectrometer;
(b) an electron emission source of electrons located in said chamber between said acceleration electrode and the point of injection of said heated spray into said chamber comprising electron-emission electrode means and power supply means connected to said electron emission electrode means; and
(c) variable power supply means electrically connected between said accelerating electrode and said sidewall of said chamber for providing a positive voltage of from about 10 to about 300 volts on said acceleration electrode with respect to the sidewall of said ionization chamber;

whereby the potential on said acceleration electrode may be adjusted at a voltage sufficiently high to permit a stream of electrons flowing from said electron emission source to said acceleration electrode to bombard said heated spray to form hydronium ions and fragment at least a portion of said molecules being analyzed into two or more lower molecular weight constituents to thereby aid in identification of said molecules.

16. The apparatus of claim 15 wherein said semispherical end of said acceleration electrode has a radius of from about 0.05 to about 0.100 inches and said acceleration electrode protrudes into said cylindrical chamber a distance of about 5 to about 50% of the diameter of said cylindrical chamber.

17. A method of analyzing a liquid eluent from a chromatograph column injected as a heated spray into an ionization chamber located between said chromatograph and a mass spectrometer to form ionized adducts containing solvent and the molecule to be analyzed which are then passed into said mass spectrometer through an exit port in the sidewall of said ionization chamber, which comprises:
(a) providing an acceleration electrode in the sidewall of said ionization chamber at a position opposite said exit port into said mass spectrometer;
(b) providing an electron emission source located between said acceleration electrode and the point of injection of said heated spray into said chamber; and (c) applying a positive voltage to said acceleration electrode with respect to said sidewall of said ionization chamber;

whereby raising said positive voltage on said acceleration electrode to a potential sufficiently high creates a stream of electrons flowing from said electron emission source to said acceleration electrode to bombard said heated spray to fragment at least a portion of said molecules being analyzed into two or more lower molecular weight constituents to thereby aid in identification of said molecules.

18. The method of claim 17 wherein said step of applying a positive voltage on said acceleration electrode further comprises applying a voltage of from about 5 to about 300 volts to create said stream of electrons in said chamber.

19. The method of claim 17 wherein said step of providing a positive voltage on said acceleration electrode further comprises the step of raising said positive voltage until the presence of hydronium ions is detected in said mass spectrometer indicative of an electron stream flowing from said electron emission source to said accelerating electrode of a sufficient energy to fragment molecules in said liquid eluent to permit formation and subsequent detection of fragments of said molecules to aid in identification of said molecules.

20. The method of claim 19 wherein said step of raising said positive voltage on said accelerating electrode further comprises raising said voltage in the range of from about 5 to about 300 volts.

* * * * *